United States Patent

Harkness et al.

[11] Patent Number: 5,502,229
[45] Date of Patent: Mar. 26, 1996

[54] DIPHENYLSILOXANE OLIGOMERS FUNCTIONALIZED AT BOTH TERMINAL AND METHOD FOR THE PREPARATION THEREOF

[75] Inventors: Brian R. Harkness; Mamoru Tachikawa; Kasumi Takeuchi, all of Kanagawa, Japan

[73] Assignee: Dow Corning Asia, Ltd., Tokyo, Japan

[21] Appl. No.: 403,991

[22] Filed: Mar. 14, 1995

[30] Foreign Application Priority Data

Mar. 23, 1994 [JP] Japan .................................. 6-052009

[51] Int. Cl.$^6$ .......................................... C07F 7/08
[52] U.S. Cl. ................................ 556/406; 556/451
[58] Field of Search ....................... 556/406, 451

[56] References Cited

U.S. PATENT DOCUMENTS

| | | | |
|---|---|---|---|
| 3,655,713 | 4/1972 | LeGrow | 556/406 |
| 3,719,696 | 3/1973 | Jonas et al. | 556/406 |
| 4,831,169 | 5/1989 | Grape et al. | 556/451 |
| 5,319,121 | 6/1994 | Blum | 556/451 X |

FOREIGN PATENT DOCUMENTS 214735  2/1991  Japan .

OTHER PUBLICATIONS

Journal of the Chemical Society of Japan, Industrial Chemistry, Section, vol. 62, p. 1421 (1959).

*Primary Examiner*—Paul F. Shaver
*Attorney, Agent, or Firm*—Alexander Weitz

[57] ABSTRACT

There is disclosed a diphenylsiloxane oligomer functionalized at both terminals, and methods for the preparation thereof, said oligomer having the following general formula G-(OSi(Ph)$_2$)$_m$O—G wherein Ph denotes a phenyl radical, m is 3 to 50 and G is has a formula independently selected from the group consisting of

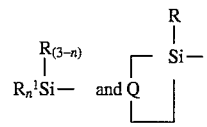

in which R$^1$ is independently selected from the group consisting of hydrogen and a monovalent hydrocarbon group having 2 to 8 carbon atoms, said monovalent hydrocarbon group excluding phenyl, tolyl, xylyl, and ethylphenyl radicals, R is independently selected from the group consisting of R$^1$, methyl radical and phenyl radical, Q is a divalent hydrocarbon group and n is an integer having a value of 1 to 3.

11 Claims, 1 Drawing Sheet

DIPHENYLSILOXANE OLIGOMERS FUNCTIONALIZED AT BOTH TERMINAL AND METHOD FOR THE PREPARATION THEREOF

FIELD OF THE INVENTION

This invention relates to diphenylsiloxane oligomers that are capped at both terminals with a silyl group having at least one substituent selected from the hydrogen atom or a $C_2$ to $C_8$ saturated or unsaturated hydrocarbon group, but excluding the phenyl, tolyl, xylyl, and ethylphenyl groups. This invention also relates to methods for the preparation of said diphenylsiloxane oligomers.

BACKGROUND OF THE INVENTION

Within the spectrum of polymeric compounds that contain diphenylsiloxane units, oligomers are known, inter alia, in the form of cyclic oligomers, siloxanes stopped at both terminals by the trimethylsilyl group, and siloxanes bearing silanol at both terminals. Examples of the cyclic oligomers are hexaphenylcyclotrisiloxane, which is the diphenylsiloxane trimer, and octaphenylcyclotetrasiloxane, which is the tetramer. These are diphenylsiloxane compounds that are fairly soluble in organic solvents and melt at between room temperature and 300° C. However, they lack chemical reactivity because they are composed of the chemically stable phenyl group and the similarly stable siloxy bond. In addition, the corresponding solids are in essence organic crystals, and as such their material strength is quite low. In consequence thereof, their exploitation as materials, either alone or in combination with other materials, is unpromising.

With regard to diphenylsiloxane oligomer capped at both terminals with trimethylsilyl, 1,1,1,9,9,9-hexamethyl- 3,3,5,5,7,7-hexaphenylpentasiloxane is known from *Journal of the Chemical Society of Japan, Industrial Chemistry Section*, Volume 62, page 1421 (1959). This is also a soluble and fusible diphenylsiloxane. But again, it is composed of the chemically stable phenyl group and the similarly stable trimethylsiloxy group and thus is extremely stable and very inert.

Diphenylsiloxane bearing silanol at both terminals is exemplified by tetraphenyldisiloxane-1,3-diol and hexaphenyltrisiloxane-1,5-diol. These, too, are soluble and fusible diphenylsiloxanes, which again are composed of the chemically stable phenyl group and the similarly stable siloxy bond. Only the silanol group may be classified as a functional group capable of readily participating in bonding. The silanol group is in general able to participate in the formulation of compositions through the formation of hydrogen bonds the functional groups in another substance or through bond formation by reaction with other hydrolyzable groups. However, when bonded to the diphenylsiloxy group, the silanol group is very inert. In addition, at high temperatures the silanol group participates in a "backbiting" reaction that is characteristic of polysiloxanes bearing this functional group. Stability then becomes a problem due to the resulting depolymerization reaction.

Moving up to the level of polymers comprising diphenylsiloxane units, the polydiphenylsiloxane homopolymers are already known. These can be prepared by the ring-opening polymerization of hexaphenylcyclotrisiloxane. These homopolymers are brittle white crystalline solids that undergo a phase transition in the vicinity of 260° C. to yield a mesophase. This mesophase exhibits poor fluidity, which makes the molding and processing of these homopolymers quite difficult. While these homopolymers could be expected to exhibit satisfactory fluiditics at temperatures above their melting points, they melt at 500° C. and above, at which temperatures they undergo thermal decomposition. Thus, rather severe problems are associated with the processing of these polymers and the formation of compositions with other materials.

The polydimethylsiloxanes are the most typical siloxanes and have various types of derivatives. Many derivatives with the structures given in formula (A) below are known. Oligomers of this class generally remain liquid even at temperatures several tens of degrees Centigrade below the freezing point and thus cannot be hot-melt molded. The polydimethylsiloxane derivatives are prepared by an equilibration reaction between cyclic polydimethylsiloxane oligomer and an end group generally known as an end blocker. However, in the case of dipenylsiloxane, the equilibrium between the cyclic oligomer and straight-chain polymer is strongly skewed toward production of the cyclic oligomer. As a result, diphenylsiloxane oligomer functionalized at both terminals (hereinafter abbreviated as diterminal-functionalized diphenylsiloxane oligomer) essentially cannot be prepared by the analogous preparative method, i.e., using an equilibration reaction.

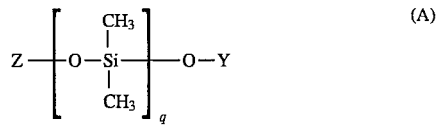

(A)

In addition to the preceding, siloxane structures described by the following formula (B) have been widely reported (for example, in Japanese Patent Application Laid Open Number Hei 5-32783). These are siloxane structures that carry various types of functional groups at the two terminals of a diphenylsiloxane-dimethylsiloxane random copolymer.

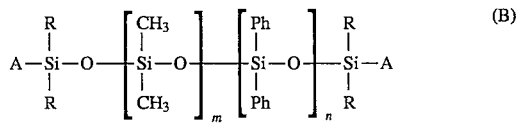

(B)

wherein m and n are integers, A is a functional group bonded to the silicon across a divalent organic group and pH hereinafter denotes a phenyl radical. The main chain in these polymers has a random copolymer structure, which results in these polymers being soluble in solvents and exhibiting fluidity when heated. These polymers, therefor, differ in their composition, properties, and preparation from the diterminal-functionalized diphenylsiloxane oligomers introduced and disclosed by the present invention. In particular, the nature of the contribution of the siloxane fraction to the physical properties of compositions is substantially different for these siloxanes, both when used alone and when used in combination with other materials.

SUMMARY OF THE INVENTION

The present invention takes as its object the introduction of diphenylsiloxane oligomers capped at both terminals by functional groups that are more reactive than the phenyl or methyl group and capable of forming intermolecular crosslinkages by crosslinking reactions. The resulting cured products can be used as corrsion-resistant coatings for metals and as insulating materials in electronic components. An additional object of the invention is the introduction of methods for preparing the described diphenylsiloxane oligomers. Examples of subject reactive functional groups are silicon-bonded hydrogen, saturated hydrocarbon groups (e.g., ethyl, propyl, isopropyl, etc.), and unsaturated hydrocarbon groups (vinyl, propenyl, allyl, etc.) in oxidizing ambients, and groups such as vinyl, propenyl, allyl, 4-vinylphenyl, silacyclobutyl, etc., under radical-reaction conditions.

The present invention has been disclosed in Japanese Laid Open Patent Application Number Hei 6-052009, the full disclose of which is hereby incorporated by reference.

DETAILED DESCRIPTION OF THE INVENTION

Figure 1:
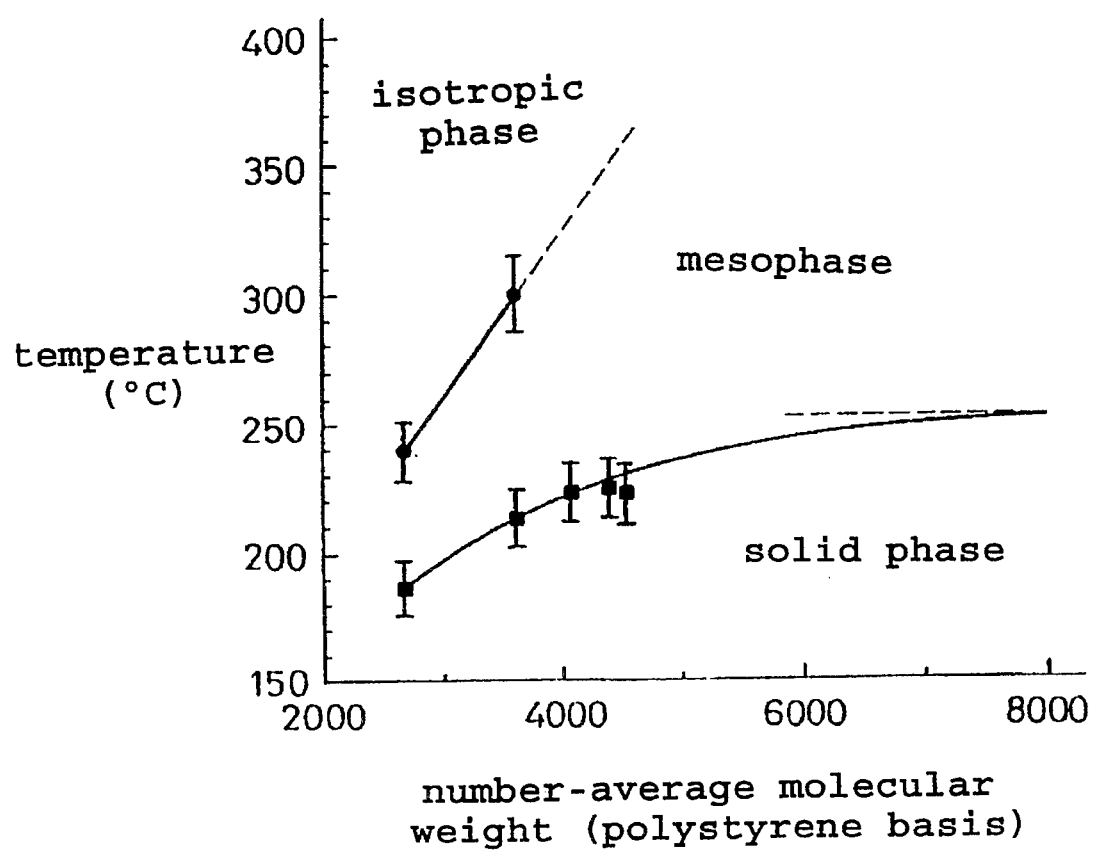
FIG. 1 shows the melting temperature of polydiphenylsiloxane polymers and oligomers as a function of their number average molecular weight.

The inventors of the instant application have observed that, for diphenylsiloxane polymers having degree of polymerization n up to approximately 50, there is a direct relationship between the degree of polymerization (DP) of the polymer (or oligomer) and its melting point as shown in FIG. 1. In other words, polymer (or oligomer) melting points between room temperature and 400° C. can be obtained through suitable selection of the degree of polymerization n. In addition, the solubility of the polymer and oligomer in organic solvent is specifically related to the degree of polymerization n. While the influence of the end group cannot be neglected, oligomer with n on the level of 3 to 6 is soluble in almost all organic solvents at room temperature. Oligomer with n from about 7 to about 11 is soluble at room temperature in polar solvents such as tetrahydrofuran, chloroform, dimethyl sulfoxide, etc., and with moderate heating also in aromatic organic compounds such as benzene, toluene, etc. At DPs from 12 to around 18, dissolution requires a solvent such as hot toluene, hot xylene, warm tetrahydrofuran, warm chloroform, or warm N-methylpyrrolidone. At DPs higher than this level, the polymer becomes almost insoluble in ordinary organic solvents. However, up to DPs of approximately 50, the polymer can still be dissolved at temperatures of 150° C. or more in polar high-boiling organic solvents, for example, phenyl ethyl, orthoterphenyl, N,N-dimethylformamide, etc. As an example, Table 1 reports the solubility in various organic solvents of diphenylsiloxane oligomer with a degree of polymerization n of approximately 8.

TABLE 1

| Solubility of Diphenylsiloxane Oligomer | | |
|---|---|---|
| Organic Solvent | Room-Temperature Solvent (25° C.) | Hot Solvent |
| tetrahydrofuran | soluble | |
| chloroform | soluble | |
| methylene chloride | soluble | |
| toluene | moderately soluble | soluble |
| dimethyl sulfoxide | insoluble | soluble |
| N,N-dimethylacetamide | insoluble | soluble |
| 1,2-dimethoxyethane | insoluble | soluble |
| n-hexane | | moderately soluble |
| ethyl acetate | | sparingly soluble |
| methyl ethyl ketone | insoluble | |
| acetone | insoluble | |
| methanol | insoluble | |

Notes:
hot solvent: 80° C. or the boiling point of the solvent (acetone, methanol, n-hexane, ethyl acetate).
soluble: denotes dissolution of approximately 10 weight % sample.
diphenylsiloxane oligomer: the octamer of diphenylsiloxane capped at both terminals with the vinyldimethylsilyl group.

Based on the preceding information, the inventors conducted research into diterminal-functionalized diphenylsiloxane oligomers with general formula (I) below and as a result were able to achieve the instant invention.

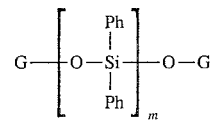

wherein G has its formula independently selected from

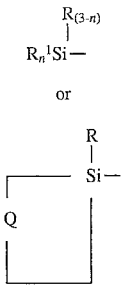

In the above formulas, $R^1$ is independently selected from the hydrogen atom or a saturated or unsaturated monovalent hydrocarbon group having 2 to 8 carbon atoms, with the proviso that $R^1$ is not phenyl, tolyl, xylyl or ethylpheny; R is selected from phenyl, methyl or $R^1$; n is an integer having a value of 1 to 3; Q represents a divalent hydrocarbon group; Ph hereinafter represents phenyl radical; and m is a number between 3 and 50 and represents the average degree of polymerization of the oligomer. Q preferably has 3 to 5 carbon atoms.

The first embodiment of the instant invention is a diterminal-functionalized diphenylsiloxane oligomer with the preceding general formula (I).

The second embodiment of the instant invention is a method for the preparation of the diterminal-functionalized diphenylsiloxane oligomers with general formula (I). This method comprises running a reaction, whose by-product is HX, between silanol-endstopped diphenylsiloxane oligomer with the following general formula (II)

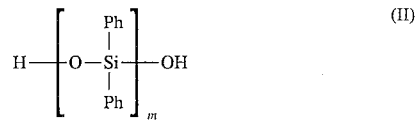

in which Ph and m are defined as above, and at least one silane having its formula selected from

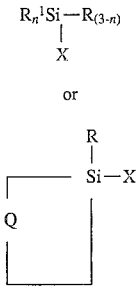

wherein $R^1$, R, Q and n have their previously defined meanings and X is independently selected from alkoxy, acyloxy, alkenoxy, amide, amino, silylated amino, chlorine, bromine or iodine groups.

The third embodiment of the instant invention is a method for the preparation of the diterminal-functionalized diphenylsiloxane oligomers with general formula (I) encompassed by the first embodiment, comprising running a reaction, whose by-product is $MX^1$, between diphenylsiloxane oligomer with the following general formula (III) that is stopped at both terminals by the lithium, sodium, or potassium silanolate group

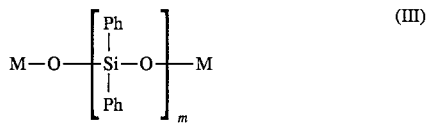

in which Ph and m are defined as above, and M represents lithium, sodium, or potassium, and at least one silane having its formula selected form

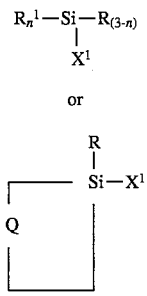

wherein $R^1$, R, Q and n have their previously defined meanings and $X^1$ is independently selected from acyloxy, chlorine, bromine or iodine groups.

The reaction in the aforementioned second and third embodiments is represented by generalized equation (IV) below. In the equation, M' denotes hydrogen, lithium, sodium, or potassium; G has the same definitions as given above; the silane is at least one of those described in the connection with the second or third embodiment, supra.

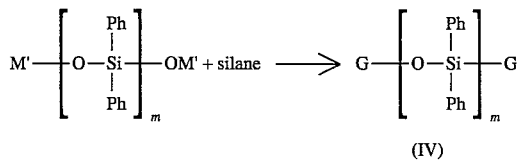

The subscript m, which denotes the average degree of polymerization of the diphenylsiloxane oligomer of the present invention, is a number from 3 to 50. The saturated and unsaturated $C_2$ to $C_8$ hydrocarbon groups which may be bonded in the terminal silyl groups are exemplified by saturated n-alkyl groups, for which typical examples are ethyl, n-propyl, n-butyl, n-pentyl, n-hexyl, n-heptyl, and n-octyl; saturated branched alkyl groups, for which typical examples are isopropyl, sec-butyl, 2-methylpropyl, tert-butyl, isopentyl, sec-hexyl, and 2-ethylhexyl; alkenyl groups such as vinyl, allyl, propenyl, isopropenyl, crotyl, hexenyl, octenyl, and so forth; alkynyl groups, for which typical examples are ethynyl, propynyl, propargyl, butynyl, and phenylethynyl; aryl groups such as 4-vinylphenyl, ethynylphenyl, etc.; aralkyl groups such as benzyl, phenethyl, etc.; and silacyclo structures in which two of the substituents are connected to give, for example, a trimethylene, tetramethylene, or pentamethylene bridge.

For the purposes of the present invention, the methyl, phenyl, tolyl, xylyl, and ethylphenyl groups are hydrocarbon groups that may not be present, either in compounds according to the invention or in starting materials used in the preparative methods, in the capacity of the saturated and unsaturated $C_2$ to $C_8$ hydrocarbon substituents specified for the preceding $R^1$ groups.

The following are examples, based on the preceding description, of the endstopping silyl groups that may be present at the two terminals of the diphenylsiloxane oligomers according to the present invention: dimethylhydrogensilyl, methyldihydrogensilyl, trihydrogensilyl, diphenylhydrogensilyl, phenyldihydrogensilyl, methylphenylhydrogensilyl, ethyldimethylsilyl, diethylmethylsilyl, triethylsilyl, ethyldiphenylsilyl, diethylphenylsilyl, ethylmethylphenylsilyl, propyldimethylsilyl, dipropylmethylsilyl, tripropylsilyl, propyldiphenylsilyl, dipropylphenylsilyl, propylmethylphenylsilyl, butyldimethylsilyl, dibutylmethylsilyl, tributylsilyl, butyldiphenylsilyl, dibutylphenylsilyl, butylmethylphenylsilyl, hexyldimethysilyl, dihexylmethylsilyl, trihexylsilyl, hexyldiphenylsilyl, dihexylphenylsilyl, hexylmethylphenylsilyl, octyldimethylsilyl, dioctylmethylsilyl, troctylsilyl, octyldiphenylsilyl, dioctylphenylsilyl, octylmethylphenylsilyl, vinyldimethylsilyl, divinylmethylsilyl, trivinylsilyl, vinyldiphenylsilyl, isopropyldimethylsilyl, diisopropylmethylsily, triisopropylsilyl, isopropyldiphenylsilyl, diisoproylphenylsilyl, isopropylmethylphenylsilyl, 2-ethylhexyldimethylsilyl, bis(2-ethylhexyl)methylsilyl, tris(2-ethylhexyl)silyl, 2-ethylhexyldiphenylsilyl, bis(2-ethylhexyl)phenylsilyl, 2-ethylhexylmethylphenylsilyl, divinylphenylsilyl, vinylmethylphenylsilyl, propenyldimethylsilyl, dipropenylmethylsilyl, tripropenylsilyl, propenyldiphenylsilyl, dipropenylphenylsilyl, propenylmethylphenylsilyl, hexenyldimethylsilyl, dihexenylmethylsilyl, trihexenylsilyl, hexenyldiphenylsilyl, dihexenylphenylsilyl, hexenylmethylphenylsilyl, ethyldimethylsilyl, diethynylmethylsilyl, triethynylsilyl, ethynyldiphenylsilyl, diethynylphenylsilyl, ethynylmethylphenylsilyl, butynyldimethylsilyl, dibutynylmethylsilyl, tributynylsilyl, butynyldiphenylsilyl, dibutynylphenylsilyl, butynylmethylphenylsilyl, (4-vinylphenyl)dimethylsilyl, bis( 4-vinylphenyl)methylsilyl, tris(4-vinylphenyl)silyl, ( 4-vinylphenyl)diphenylsilyl, bis(4-vinylphenyl)phenylsilyl, (4-vinylphenyl)methylphenylsilyl, (ethynylphenyl)dimthylsilyl, di(ethynylphenyl)methylsilyl, tri(ethynylphenyl)silyl, (ethynylphenyl)diphenylsilyl, di(ethynylphenyl)phenylsilyl, (ethynylphenyl)methylphenylsilyl, benzyldimethylsilyl, divinylmethylsilyl, tribenzylsilyl, benzyldiphenylsilyl, dibenzylphenylsilyl, benzylmethylphenylsilyl, butylvinylmethylsilyl, butylethylmethylsilyl, butylethylphenylsilyl, butylvinylphenylsilyl, allylvinylphenylsilyl, allylmethylphenylsilyl, allyldimethylsilyl, diallylmethylsilyl, triallylsilyl, allyldiphenylsilyl, diallylphenylsilyl, allylmethylphenylsilyl, 1-(1-methylsilacyclobutyl), 1-(1-methylsilacyclopentyl), 1-(1-methylsilacyclohexyl), 1-(1-phenylsilacyclobutyl), 1-( 1-phenylsilacyclopentyl), 1-(1-phenylsilacyclohexyl), 1-( 1-ethylsilacyclobutyl), 1-(1-ethylsilacyclopentyl), 1-( 1-ethylsilacyclohexyl), and so forth.

The diphenylsiloxane oligomer carrying silanol at both terminals, as described by general formula (II) above, is exemplified by individual compounds such as hexaphenyltrisiloxane-1,5-diol and octaphenyltetrasiloxane-1,7-diol and by mixtures of members of this series wherein the average degree of polymerization is m, as defined above.

EXAMPLES

The invention is explained in greater detail below through working and reference examples, but the invention is not thereby limited. In the product characterization data reported in the examples, $^1$H NMR refers to proton nuclear magnetic resonance spectroscopy, $^{13}$C {1H} NMR refers to proton-decoupled $^{13}$C nuclear magnetic resonance spectroscopy, and $^{29}$Si {1H} NMR refers to proton-decoupled $^{29}$Si nuclear magnetic resonance spectroscopy. CDCl$_3$ refers to deuterochloroform. In the proton nuclear magnetic resonance spectroscopic data, the s, d, t, and m reported in parentheses indicate, respectively, singlet, doublet, triplet, and multiplet. 1H, 2H, 3H, etc., refer, respectively, to a spectral integral ratio corresponding to 1 proton, 2 protons, 3 protons, etc. The chemical shifts in the nuclear magnetic resonance spectra are in all cases reported using 0 ppm for tetramethylsilane. GC-MS refers to gas chromatography-mass spectrometric analysis, and GPC refers to gel permeation chromatography. Unless stated otherwise, parts denotes weight parts.

REFERENCE EXAMPLE 1

Synthesis of hexaphenyltrisiloxane-1,5-diol 55 parts of hexaphenylcyclotrisiloxane was dissolved in 400 parts of tetrahydrofuran in an Erlenmeyer flask. 3 parts of hexylamine and 40 parts of water were then introduced, and the reaction was stirred for 30 minutes at room temperature. After confirmation by thin-layer chromatography of conversion to the diol, the reaction solution was poured into 500 parts of water and neutralized with dilute hydrochloric acid. The organics were extracted with 600 parts toluene. After washing this several times with water, drying over anhydrous sodium sulfate, filtration, and concentration of the filtrate to 150 parts on a rotary evaporator, the addition of hexane yielded crystalline hexaphenyltrisiloxane-1,5-dol in a yield of 93%.

Analysis of hexaphenyltrisiloxane-1,5-diol: melting point=110°–111° C.; infrared absorption at 3244 cm$^1$.

REFERENCE EXAMPLE 2

Synthesis of (4-vinylphenyl)dimethylchlorosilane (4-Vinylphenyl)magnesium chloride was synthesized by the gradual dropwise addition of 50 parts of p-chlorostyrene to a mixture of 15 parts magnesium turnings and 100 parts tetrahydrofuran. This was gradually added dropwise over 2 hours to 50 parts of dimethyldichlorosilane dissolved in 100 parts tetrahydrofuran, after which the reaction was heated for an additional 1 hour under reflux. The reaction solution was cooled and then filtered and the solvent was distilled off. Distillation of the residual liquid at 1 mmHg yielded 50 parts of 4 vinylphenyldimethylchlorosilane. The product was identified by mass spectrometric analysis and $^1$H-, $^{13}$C-, and $^{29}$Si-NMR spectroscopy.

REFERENCE EXAMPLE 3

Synthesis of (phenylethynyl)dimethylchlorosilane

A suspension of phenylethynyllithium was prepared by the dropwise addition over 1 hour of 16 parts of a 1.0 mol/L solution of n-butyllithium in hexane to 23 parts of phenylacetylene dissolved in 100 parts of ethyl ether. This suspension was gradually added dropwise over a period of 1 hour to a mixture of 60 parts dimethyldichlorosilane and 100 parts ether. After removal of the lithium chloride by filtration, distillation of the filtrate yielded 30 parts phenylethynyldimethylchlorosilane.

Analysis of the phenylethynyldimethylchlorosilane:

$^1$H-NMR (CDCl$_3$) 0.65 (s, 6H), 7.3–7.53 (m, 5H).

$^{13}$C {1H}-NMR (CDCl$_3$) 3.74, 89.67, 106.87, 121.76, 128.30, 129.39, 132.16.

$^{29}$Si {1H}-NMR (CDCl$_3$) 0.40 ppm.

REFERENCE EXAMPLE 4

Synthesis of 1-phenyl-1-chlorosilacyclopentane

A mixture of 25 parts of 1,4-dibromobutane and 50 parts of tetrahydrofuran was added dropwise over a period of 2 hours to a mixture of 200 parts of tetrahydrofuran, 80 parts phenylmethyldichlorosilane, and 25 parts of magnesium turnings. The reaction solution was heated under reflux for 1 hour, and the magnesium salt was then removed by filtration. Vacuum distillation of the filtrate subsequently yielded 20 parts 1-phenyl- 1-chlorosilacyclopentane.

Analysis of the 1-phenyl-1-chlorosilacyclopentane:

$^1$H-NMR (CDCl$_3$) 1.145 (t, 4H), 1.77 (m, 2H), 1.90 (m, 2H), 7.4–7.7 (m, 5H).

REFERENCE EXAMPLE 5

Synthesis of diallylmethylchlorosilane

Allylmagnesium chloride was synthesized by the gradual dropwise addition of 50 parts of allyl chloride to a mixture of 15 parts of magnesium turnings and 100 parts of tetrahydrofuran. This was gradually added dropwise over a period of 2 hours to 18 parts of methyldichlorosilane dissolved in 100 parts of tetrahydrofuran, and the reaction was then heated for an additional 1 hour under reflux. After cooling the reaction, the solution was filtered, the solvent was distilled off, and the residual liquid was distilled at 1 mmHg. 15 parts of diallylmethylsilane was obtained. The silicon-bonded hydrogen in this compound was replaced by chlorine by a standard method. Distillation then yielded the target compound.

Diallylmethylchlorosilane:

$^1$H-NMR (CDCl$_3$) 0.39 (3H, s), 1.83 (m, 4H), 4.95 (m, 2H), 5.00 (m, 2H), 5.76 (m, 2H).

$^{13}$C {1H}-NMR (CDCl$_3$) −1.12, 24.49, 115.63, 131.71.

$^{29}$Si {1H}-NMR (CDCl$_3$) −24.9 ppm.

REFERENCE EXAMPLE 6

Synthesis of 1-chloro-1-methylsilacyclobutane

This entire procedure was run under dry nitrogen. 18.2 parts of magnesium turnings was first added to 250 parts of thoroughly dried tetrahydrofuran. 1 parts of dibromoethane was then added, and heating under reflux was carried out for 15 minutes. After initiating the reaction by the dropwise addition of a small amount of (3-chloropropyl)dichloromethylsilane, a mixture of 200 parts of tetrahydrofuran and 41.7 parts of (3-chloropropyl)dichloromethylsilane was slowly added dropwise. The reaction mixtures was then stirred overnight, after which the volatiles were collected by vacuum distillation. This was subjected to precision distillation to obtain 1-chloro-1-methylsilcyclobutane in a yield of 64%.

Analysis of the 1-chloro-1-methylsilyclobutane:

GC-MS: m/z=122, 120, 94, 92, 65.

$^1$H-NMR (CDCl$_3$), 0.63 (s, 3H), 1.42 (m, 4H), 2.20 (m, 2H).

$^{13}$C {1H}-NMR (CDCl$_3$) 3.52, 15.8, 20.7.

EXAMPLE 1

Synthesis of oligo(diphenylsiloxane) stopped at both terminals by the vinyldimethylsilyl group Ten parts of vinyldimethylchlorosilane and 10 parts of triethylamine were added to 20 parts of hexaphenyltrisiloxane-1,5-diol (synthesis described in Reference Example 1) dissolved in 100 parts of toluene, and the mixture was stirred for 1 hour at room temperature. The reaction mixture was then slowly added to 150 parts of water and a white precipitate was produced. After the addition of 100 parts of water, the organic layer was separated, washed with water several times, and dried over anhydrous sodium sulfate. Filtration, followed by distillation of the organic solvent, gave 24.4 parts of a colorless oil. This oily product gradually crystallized.

Analytic results: infrared spectrum; a peak at 1408 cm$^{-1}$ corresponding to the vinyl group was observed.

$^1$H-NMR spectrum: 0 ppm (methyl group), 5.5–5.6 ppm (vinyl group), 7.1–7.5 (phenyl group).

EXAMPLE 2

Synthesis of hexaphenyltrisiloxane stopped at both terminals by the triethylsilyl group The dilithium salt of hexaphenyltrisiloxane-1,5-diol was prepared by the addition of 7 parts of a 1.78 mol/L hexane solution of n-butyllithium to 10 parts of hexaphenyltrisiloxane-1,5-diol (synthesis described in Reference Example 1) dissolved in 23 parts of tetrahydrofuran. 3.3 parts of triethylchlorosilane was then added at room temperature, followed by heating for 2 hours under reflux. The reaction mixture was poured into cold water, and the organics were extracted with toluene. After this toluene extract had been thoroughly washed with water, the solvent was eliminated to yield 5.95 parts of hexaphenyltrisiloxane stopped at both terminals by the triethylsilyl group in the form of an oil.

Analytic results:

$^1$H-NMR spectrum: 0.7 ppm (triplet, methyl group), 0.4 ppm (quartet, methylene group), 7.1–7.5 (phenyl group).

EXAMPLE 3

Synthesis of hexaphenyltrisiloxane stopped at both terminals by the (4-vinylphenyl)dimthylsilyl group The dilithium salt of hexaphenyltrisiloxane-1,5-diol was prepared by the addition of 27 parts of a hexane solution of n-butyllithium (1.9 mol/L) to 20 parts of hexaphenyltrisiloxane-1,5-diol (synthesis described in Reference Example 1) dissolved in 45 parts of tetrahydrofuran. To this was added at room temperature, 15 parts of (4-vinylphenyl)dimethylchlorosilane (synthesis described in Reference Example 2), followed by heating for 1.5 hours under reflux at 65° C. The unreacted silanol groups were then silylated by the addition of trimethylchlorosilane and triethylamine (1 part each). The reaction mixture was thereafter poured into 200 parts of cold water, and the organics were extracted with 300 parts of toluene. After this toluene extract had been thoroughly washed with water, the solvent was eliminated to yield 26 parts of hexaphenyltrisiloxane stopped at both terminals by the (4-vinylphenyl)dimethylsilyl group in the form of an oil.

Analytic results: infrared spectrum: residual silanol was not observed.

$^1$H-NMR spectrum: 0.1 ppm (methyl group), 5.2, 5.7, 6.7 ppm (vinyl group), 7.1–7.5 (phenyl group).

EXAMPLE 4

Synthesis of hexaphenyltrisiloxane stopped at both terminals with the dimethylsilyl group 1.1 parts of 1,1,3,3-tetramethyldisilazane and 0.8 part of dimethylchlorosilane were added to 5 parts of hexaphenyltrisiloxane-1,5-diol (synthesis described in Reference Example 1) dissolved in 20 parts of toluene, and the mixture was stirred for 1 hour at room temperature. The reaction mixture was then slowly added to 150 parts of water and a white precipitate was produced. After the addition to this of 100 parts of water, the organic layer was separated, washed with water several times, and dried over anhydrous sodium sulfate. Filtration followed by distillation of the organic solvent gave 6 parts of a colorless oil.

Analytic results: infrared spectrum: a peak corresponding to the Si-H group was observed at 2131 cm$^{-1}$.

$^1$H-NMR spectrum: 0 ppm (doublet, methyl group), 4.7 ppm (heptet, Si-H group), 7.1–7.5 (phenyl group).

EXAMPLE 5

Synthesis of hexaphenyltrisiloxane stopped at both terminals by the (1-phenyl)cyclotetramethylenesilyl group The dilithium salt of hexaphenyltrisiloxane-1,5-diol was prepared by the addition of 14 parts of a 15% hexane solution of n-butyllithium to 10 parts of hexaphenyltrisiloxane-1,5-diol (synthesis described in Reference Example 1) dissolved in 100 parts of tetrahydrofuran. To this was added at room temperature 7 parts of 1-phenyl-1-chlorosilacyclopentane (Reference Example 4), followed by stirring for 2 hours while heating at 65° C. After the reaction mixture had then been cooled to room temperature, the resulting lithium salt was removed by filtration ad 100 parts of ethyl ether was added to the filtrate. The organic layer was subsequently washed 3 times with water. Removal of the ether layer using a rotary evaporator yielded 12 parts oligo(diphenylsiloxane) stopped at both terminals by the (1-phenyl)cyclotetramethylenesilyl group.

Analytic results: NMR:

$^1$H-NMR (CDCl$_3$) 0.5–0.6 (m, 8H), 1.4–1.5 (m, 8H), 7.12–7.50 (m, 40H).

$^{29}$Si {1H}-NMR (CDCl$_3$) 15.38, −45.85, −46.17,

EXAMPLE 6

Synthesis of oligo(diphenylsiloxane) stopped at both terminals by the octenyldimethylsilyl group The following were introduced into a reactor and heated under reflux while stirring: 1.1 parts diphenylsilanediol, 10 parts of hexaphenylcyclotrisiloxane, 8.7 parts of orthoxylene, and 0.5 part of tetrahydrofuran. 2.0 parts of a 1.87 mol/L hexane solution of n-butyllithium was then added dropwise. Heating for an additional 2 hours yielded alpha, omega-dihydroxy oligo(diphenylsiloxane). To this was added 1.5 parts of 1-octenyldimethylchlorosilane and 1 part of triethylamine, and the resulting mixture was heated under reflux for 10 minutes while stirring. The reaction mixture was thereafter cooled to room temperature and then slowly added to 300 parts of vigorously stirred methanol to produce a white precipitate. The precipitate was washed with 200 parts of acetone, filtered, and dried to give 4.5 parts of oligo(diphenylsiloxane) stopped at both terminals by the (1-octenyl)dimethylsilyl group. The average molecular weight by GPC analysis was 1,900, and the molecular weight distribution ($M_w/M_n$) was 1.18. Absorption due to silanol was not observed in the infrared spectrum.

EXAMPLE 7

Synthesis of hexaphenyltrisiloxane stopped at both terminals with the (phenylethynyl)dimthylsilyl group The dilithium salt of hexaphenyltrisiloxane-1,5-diol was prepared by the addition of 14 parts of a 15 weight % hexane solution of n-butyllithium to 10 parts of hexaphenyltrisiloxane- 1,5-diol (synthesis described in Reference Example 1) dissolved in 36 parts of tetrahydrofuran. To this was then added, over a period of 5 minutes and at room temperature, 7.6 parts of (phenylethynyl)dimethylchlorosilane (Reference Example 3), followed by heating for 2 hours at 65° C. while stirring. The reaction mixture was thereafter added to a large volume of water, and the organics were extracted therefrom with toluene. The toluene solution was washed several times with distilled water, and the toluene was then removed using a rotary evaporator to yield 16.4 parts of hexaphenyltrisiloxane stopped at both terminals with the (phenylethynyl)dimethylsilyl group. This product was approximately 84% pure by GPC analysis. A strong absorption originating with the acetylene group was observed at 2160 $cm^{-1}$ in the infrared absorption spectrum.

EXAMPLE 8

Synthesis of hexaphenyltrisiloxane stopped at both terminals by the diallylmethylsilyl group The dilithium salt of hexaphenyltrisiloxane-1,5-diol was prepared by the addition of 3 parts of a 15% hexane solution of n-butyllithium to 3.0 parts of hexaphenyltrisiloxane-1,5-diol (synthesis described in Reference Example 1) dissolved in 9 parts of tetrahydrofuran. To this was then added at room temperature 1.6 parts of diallylmethylchlorosilane (Reference Example 5), followed by heating for 2 hours at 65° C. while stirring. The reaction mixture was thereafter cooled to room temperature, and the resulting lithium salt was removed by filtration. 100 parts of ethyl ether was added to the filtrate, and the organic layer was washed 3 times with water. The ether layer was removed using a rotary evaporator to yield 2.9 parts of oligo(diphenylsiloxane) stopped at both terminals by the diallylmethylsilyl group.

Analytic results: NMR:
$^1$H-NMR CDCl$_3$) −0.06 (s, 6H), 1.45 (m, 8H), 4.74 (m, 8H), 5.57 (m, 4H), 7.19–7.55 (m, 30H).
$^{29}$Si {1H}-NMR (CDCl$_3$) 3.72–46.44, −46.76.

EXAMPLE 9

Synthesis of oligo(diphenylsiloxane) stopped at both terminals by the dimethylhydrogensilyl group The following were added to a reactor and heated under reflux while stirring: 1.06 parts of diphenylsilanediol, 10 parts of hexaphenylcyclotrisiloxane, 8.7 parts ortho-xylene, and 0.5 part of tetrahydrofuran. 2.0 parts of a 1.7 mol/L hexane solution of n-butyllithium was then added dropwise. After heating for an additional two hours, 2 parts dimethylchlorosilane was added and then 1 parts of triethylamine. After cooling, the reaction solution was added to 200 parts of methanol with the formation of a precipitate. The precipitate was washed with 200 parts of acetone, filtered, and dried to give 4.9 parts of oligo(diphenylsiloxane) stopped at both terminals by the dimethylsilyl group. The average molecular weight by GPC analysis was 1,700, and the molecular weight distribution ($M_w/M_n$) was 1.16, Si-H stretching vibration was observed at 2131 $cm^{-1}$ in the infrared absorption spectrum, but absorption due to silanol was not observed.

EXAMPLE 10

Synthesis of hexaphenyltrisiloxane stopped at both terminals by the methyl(cyclotrimethylene)silyl group The dilithium salt of hexaphenyltrisiloxane-1,5-diol was prepared by the addition of 12 parts of a 15 weight % hexane solution of n-butyllithium to 8.5 parts of hexaphenyltrisiloxane- 1,5-diol (synthesis described in Reference Example 1) dissolved in 30 parts of tetrahydrofuran. To this was then added at room temperature 4.5 parts of 1-chloro-1-methylsilacyclobutane (Reference Example 6), followed by heating for 2 hours at 65° C. while stirring. The reaction mixture was thereafter cooled to room temperature and the resulting lithium salt was eliminated by filtration. The solvent was eliminated at reduced pressure, and the residue was extracted 3 times with 70 parts of hexane. Removal of the hexane on a rotary evaporator yielded 8.6 parts of oligo-(diphenylsiloxane) stopped at both terminals with the methyl(cyclotrimethylene)silyl group.

Analytic results: NMR:
$^1$H-NMR (CDCl$_3$) 0.15 (s, 6H), 1.1 (m, 8H), 1.58 (m, 2H), 2.20 (m, 2H), 7.2–7.7 (m, 30H).
$^{13}$C {1H}-NMR (CDCl$_3$, ppm) 0.75, 13.5, 20.5, 127.9–135.5.
$^{29}$Si {1H}-NMR (CDCl$_3$, ppm) −46.2, −46.0, 7.3.

That which is claimed is:

1. A diphenylsiloxane oligomer functionalized at both terminals, said oligomer having the following general formula

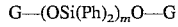

wherein Ph denotes a phenyl radical, m is 3 to 50 and G has a formula independently selected from the group consisting of

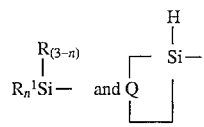

in which $R^1$ is independently selected from the group consisting of hydrogen and a monovalent hydrocarbon group having 2 to 8 carbon atoms excluding phenyl, tolyl, xylyl, and ethylphenyl radicals, R is independently selected from the group consisting of $R^1$, methyl radical and phenyl radical, Q is a divalent hydrocarbon group and n is an integer having a value of 1 to 3.

2. The diphenylsiloxane oligomer according to claim 1, wherein G is selected from the group consisting of dimethylhydrogensilyl, methyldihydrogensilyl, trihydrogensilyl, diphenylhydrogensilyl, phenyldihydrogensilyl and methylphenylhydrogensilyl.

3. The diphenylsiloxane oligomer according to claim 1, wherein G is selected from the group consisting of ethyldimethylsilyl, diethylmethylsilyl, triethylsilyl, ethyldiphenylsilyl, diethylphenylsilyl, ethylmethylphenylsilyl, propyldimethylsilyl, dipropylmethylsilyl, tripropylsilyl, propyldiphenysilyl, dipropylphenylsilyl, propylmethylphenylsilyl, butyldimethylsilyl, dibutylmethylsilyl, tributylsilyl, butyldiphenylsilyl, dibutylphenylsilyl, butylmethylphenylsilyl, hexyldimethylsilyl, dihexylmethylsilyl, trihexylsilyl, hexyldiphenylsilyl, dihexylphenylsilyl, hexylmethylphenylsilyl, octyldimethylsilyl, dioctylmethylsilyl, trioctylsilyl, octyldiphenylsilyl, dioctylphenylsilyl and octylmethylphenylsilyl.

4. The diphenylsiloxane oligomer according to claim 1, wherein G is selected from the group consisting of vinyldimethylsilyl, divinylmethylsilyl, trivinylsilyl, divinylphenylsilyl, vinylmethylphenylsilyl, vinyldiphenylsilyl, butylvinylmethylsilyl, butylvinylphenylsilyl, allylvinylphenylsilyl, allylmethylphenylsilyl, allyldimethylsilyl, diallylmethylsilyl, triallylsilyl, allyldiphenylsilyl, diallylphenylsilyl and allylmethylphenylsilyl.

5. The diphenylsiloxane oligomer according to claim 1, wherein G is selected from the group consisting of isopropyldimethylsilyl, diisopropylmethylsilyl, triisopropylsilyl, isopropyldiphenylsilyl, diisoproylphenylsilyl, isopropylmethylphenylsilyl, 2-ethylhexyldimethylsilyl, bis(2-ethylhexyl)methylsilyl, tris(2-ethylhexyl)silyl, 2-ethylhexyldiphenylsilyl, bis(2-ethylhexyl)phenylsilyl and 2-ethylhexylmethylphenylsilyl.

6. The diphenylsiloxane oligomer according to claim 1, wherein G is selected from the group consisting of propenyldimethylsilyl, dipropenylmethylsilyl, tripropenylsilyl, propenyldiphenylsilyl, dipropenylphenylsilyl, propenylmethylphenylsilyl, butylethylmethylsilyl, butylethylphenylsilyl, hexenyldimethylsilyl, dihexenylmethylsilyl, trihexeneylsilyl, hexenyldiphenylsilyl, dihexenylphenylsilyl and hexenylmethylphenylsilyl.

7. The diphenylsiloxane oligomer according to claim 1, wherein G is selected from the group consisting of ethynyldimethylsilyl, diethynylmethylsilyl, triethynylsilyl, ethynyldiphenylsilyl, diethynylphenylsilyl, ethynylmethylphenylsilyl, butynyldimethylsilyl, dibutynylmethylsilyl, tributynylsilyl, butynyldiphenylsilyl, dibutynylphenylsilyl and butynylmetylphenylsilyl.

8. The diphenylsiloxane oligomer according to claim 1, wherein G is selected from the group consisting of (4-vinylphenyl)dimethylsilyl, bis(4-vinylphenyl)methylsilyl, tris(4-vinylphenyl)silyl, (4-vinylphenyl)diphenylsilyl, bis(4-vinylphenyl)phenylsilyl, and (4-vinylphenyl)methylphenylsilyl.

9. The diphenylsiloxane oligomer according to claim 1, wherein G is selected from the group consisting of (ethynylphenyl)dimthylsilyl, di(ethynylphenyl)methylsilyl, tri(ethynylphenyl)silyl, (ethynylphenyl)diphenylsilyl, di(ethynylphenyl)phenylsilyl and (ethynylphenyl)methylphenylsilyl.

10. The diphenylsiloxane oligomer according to claim 1, wherein G is selected from the group consisting of benzyldimethylsilyl, dibenzylmethylsilyl, tribenzylsilyl, benzyldiphenylsilyl, dibenzylphenylsilyl and benzylmethylphenylsilyl.

11. A diphenylsiloxane oligomer functionalized at both terminals, said oligomer having the following general formula $$G-(OSi(P)_2)_m O-G$$

wherein Ph denotes a phenyl radical, m is 3 to 50 and G is selected from the group consisting of 1-(1-methylsilacyclopentyl), 1-(1-methylsilacyclohexyl), 1-(1-phenylsilacyclopentyl), 1-(1-phenylsilacyclohexyl), 1-(1-ethylsilacyclopentyl) and 1-(1-ethylsilacyclohexyl).

* * * * *